US010617783B2

(12) United States Patent
Leonaggeo

(10) Patent No.: US 10,617,783 B2
(45) Date of Patent: Apr. 14, 2020

(54) AIR PURIFICATION ASSEMBLY AND METHOD OF USING SAME

(71) Applicant: SCIENTIFIC AIR MANAGEMENT, LLC, Pompano Beach, FL (US)

(72) Inventor: Dana Leonaggeo, Pompano Beach, FL (US)

(73) Assignee: Scientific Air Management, LLC, Pompano Beach, FL (US)

( * ) Notice: Subject to any disclaimer, the term of this patent is extended or adjusted under 35 U.S.C. 154(b) by 0 days.

(21) Appl. No.: 16/271,266

(22) Filed: Feb. 8, 2019

(65) Prior Publication Data

US 2019/0201573 A1 Jul. 4, 2019

Related U.S. Application Data

(63) Continuation of application No. 14/872,613, filed on Oct. 1, 2015, now Pat. No. 10,226,546.

(60) Provisional application No. 62/155,630, filed on May 1, 2015.

(51) Int. Cl.
*B01D 53/02* (2006.01)
*A61L 9/20* (2006.01)
*B01D 53/04* (2006.01)

(52) U.S. Cl.
CPC ............ *A61L 9/20* (2013.01); *B01D 53/0407* (2013.01); *A61L 2209/11* (2013.01); *A61L 2209/12* (2013.01); *A61L 2209/14* (2013.01); *A61L 2209/22* (2013.01); *B01D 2253/102* (2013.01); *B01D 2257/91* (2013.01); *B01D 2259/4508* (2013.01); *B01D 2259/804* (2013.01)

(58) Field of Classification Search
CPC ............ A61L 9/2015; B01D 2253/102; B01D 2257/91; B01D 2259/4508; B01D 2259/804; B01D 53/0407
See application file for complete search history.

(56) References Cited

U.S. PATENT DOCUMENTS

| 5,523,057 | A  | 4/1996  | Mazzilli   |
|-----------|----|---------|------------|
| 6,358,374 | B1 | 3/2002  | Obee       |
| 6,464,760 | B1 | 10/2002 | Sham       |
| 8,017,073 | B2 | 9/2011  | Engelhard  |
| 8,277,735 | B2 | 10/2012 | Engelhard  |
| 8,734,724 | B2 | 5/2014  | Engelhard  |
| 2005/0287051 | A1 | 12/2005 | Yuen    |
| 2010/0196222 | A1 | 5/2010  | Kosugi  |
| 2010/0111792 | A1 | 6/2010  | Nelson  |
| 2011/0126828 | A1 | 2/2011  | Wu      |
| 2013/0142692 | A1 | 6/2013  | Tarifi  |
| 2014/0146519 | A1 | 5/2014  | Chang   |

(Continued)

*Primary Examiner* — Christopher P Jones
(74) *Attorney, Agent, or Firm* — Duane Morris LLP; Gregory M. Lefkowitz

(57) ABSTRACT

An air purification assembly is described. The air purification assembly includes an intake portion, a flow apparatus coupled to the intake portion; and a chamber portion coupled to the flow apparatus. The intake portion includes a surface and at least one first opening in the surface such that the intake portion is enabled to receive contaminated air flow through the at least one first opening. The chamber portion includes at least one second opening and further comprises an activated nonmetallic element and an ultraviolet (UV) light assembly. The flow apparatus is adapted to draw contaminated air into the air purification assembly through the at least one first opening and direct the contaminated air out of the air purification assembly through the second openings.

20 Claims, 13 Drawing Sheets

(56) References Cited

U.S. PATENT DOCUMENTS

| | | |
|---|---|---|
| 2015/0030506 A1 | 1/2015 | Kao |
| 2015/0033942 A1 | 5/2015 | Zhang |
| 2015/0064069 A1 | 5/2015 | Yi |
| 2015/0297771 A1 | 10/2015 | Law |
| 2016/0045866 A1 | 2/2016 | Wang |
| 2016/0272836 A1 | 9/2016 | Czaplik |
| 2016/0129432 A1 | 12/2016 | Ozaki |

AIR PURIFICATION ASSEMBLY AND METHOD OF USING SAME

CROSS-REFERENCE TO RELATED APPLICATIONS

This application is a continuation of U.S. Non-Provisional Patent Application Ser. No. 14/872,613, filed Oct. 1, 2015, which claims priority to U.S. Provisional Patent Application No. 62/155,630, filed May 1, 2015, the entireties of which are incorporated herein by reference.

BACKGROUND

Air handling systems are used in a wide variety of settings for various purposes, including cooling, odor elimination, filtering, and pathogen elimination. Many air handling systems are adapted for air purification. However, there is generally a trade-off between elimination of pathogens and treatment rate (i.e., flow rate). The result has been costly and complex air purification devices that are difficult to maintain and too costly for some applications.

SUMMARY OF THE INVENTION

In one embodiment, an air purification assembly is provided. The air purification assembly can include an intake portion comprising a surface and at least one first opening in the surface such that the intake portion is enabled to receive contaminated air flow through the at least one first opening; a flow apparatus coupled to the intake portion; and a chamber portion coupled to the flow apparatus. The chamber portion can include at least one second opening, where the chamber portion also includes an activated nonmetallic element and an ultraviolet (UV) light assembly. The flow apparatus can be adapted to draw contaminated air into the air purification assembly through the at least one first opening and direct the contaminated air out of the air purification assembly through the second openings.

In another embodiment, the air purification assembly can include an intake portion comprising a surface and a plurality of first openings defined on the surface such that the intake portion is enabled to receive contaminated air flow through the plurality of first openings; a flow apparatus coupled to the intake portion, wherein the flow apparatus is configured to facilitate efficient channeling of the contaminated air flow through the air purification assembly; and a chamber portion coupled to the flow apparatus. The chamber portion can include a plurality of second openings, and the chamber portion can also include activated charcoal and a ultraviolet (UV) light assembly to enable the chamber portion to purify the contaminated air flow when the contaminated air flow is channeled through the chamber portion such that decontaminated air flow is channeled through the plurality of second openings. The UV light assembly can include a UV light source that extends from a first end of the chamber portion to a second end of the chamber portion; a conduit coupled to the UV light source, the conduit configured to channel electrical current to the UV light source; and a control device coupled to the UV light source via the conduit. The control device can be configured to control the amount of electrical current being channeled to and being used by the UV light source.

DETAILED DESCRIPTION

The assembly and method described herein provide a portable air purification assembly that can be used in various types of systems, living spaces, or vehicles, such as cars, boats, and/or airplanes. The air purification assembly has several portions or components, such as an intake portion for receiving contaminated air flow, a flow apparatus for efficiently directing the contaminated air flow through the assembly, a chamber portion containing an ultraviolet (UV) light assembly, and an activated nonmetallic element, such as charcoal, to purify or decontaminate the air flow. As such, the air flow exiting or leaving the air purification assembly is decontaminated air flow.

Figure 1:
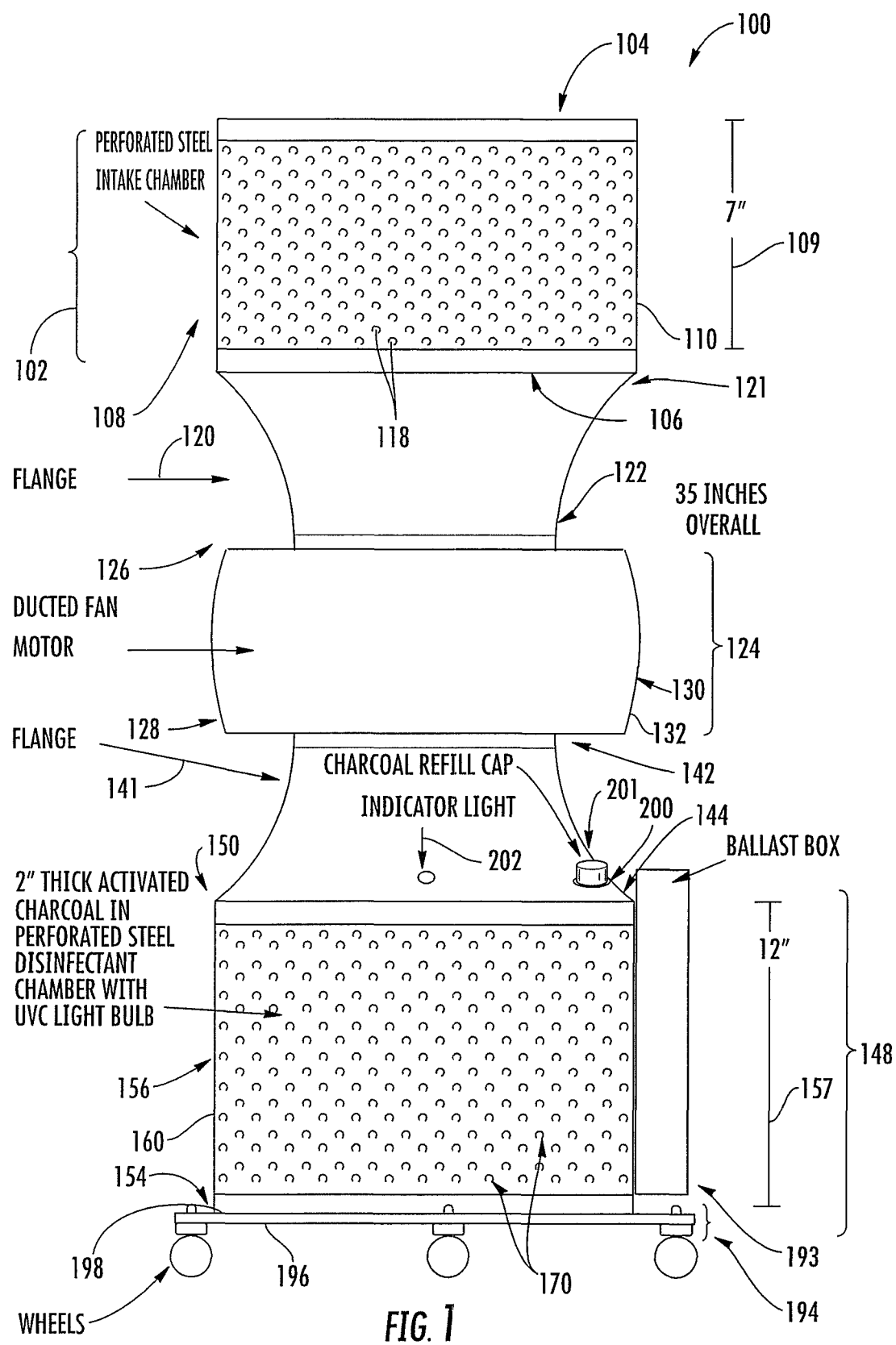
FIG. 1 is a front view of an air purification assembly as described herein.
Figure 2:
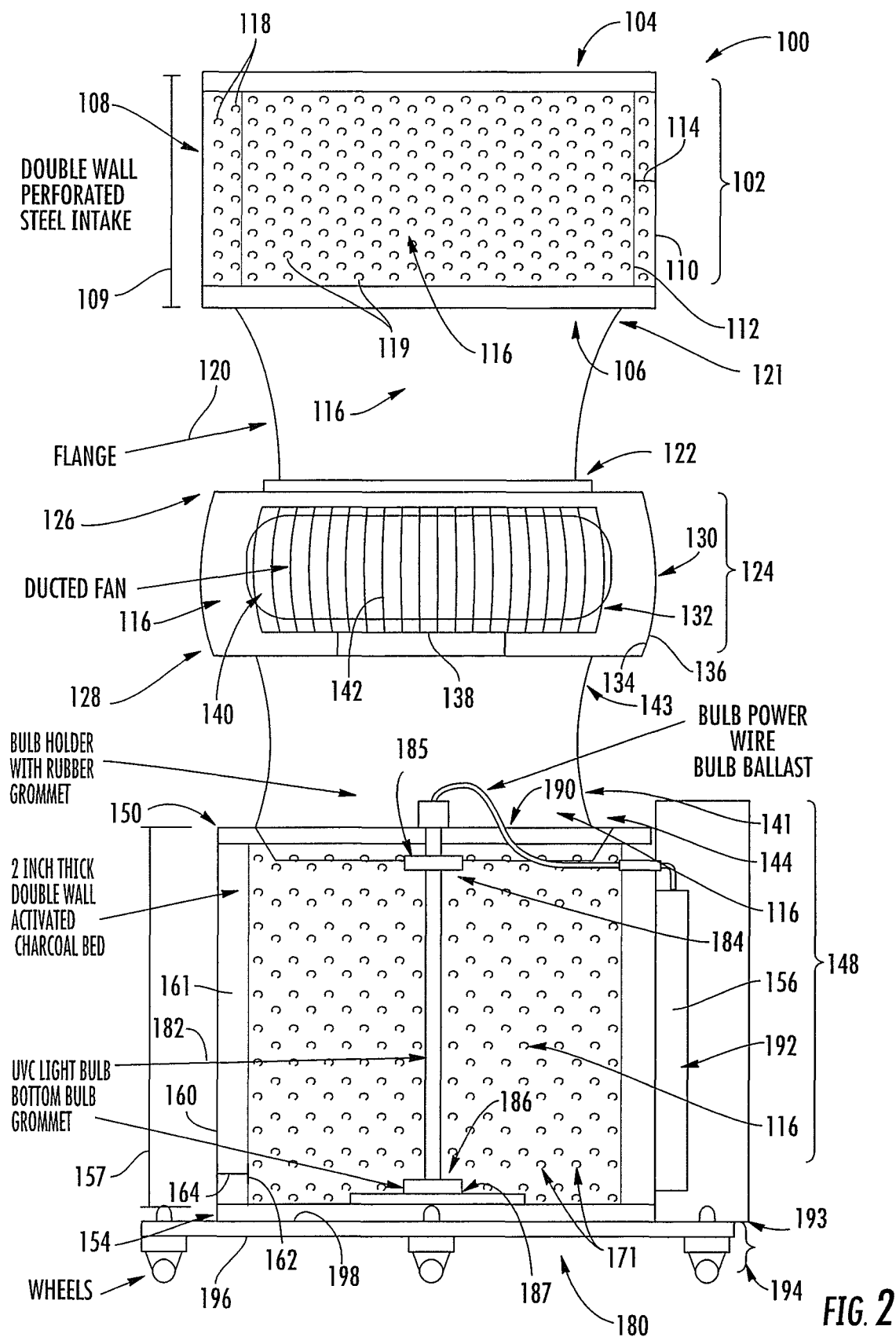
FIG. 2 is a cross-sectional view of a portion of the air purification assembly shown in FIGS. 1 & 3 taken along cut line 2-2 of FIG. 3.
Figure 3:
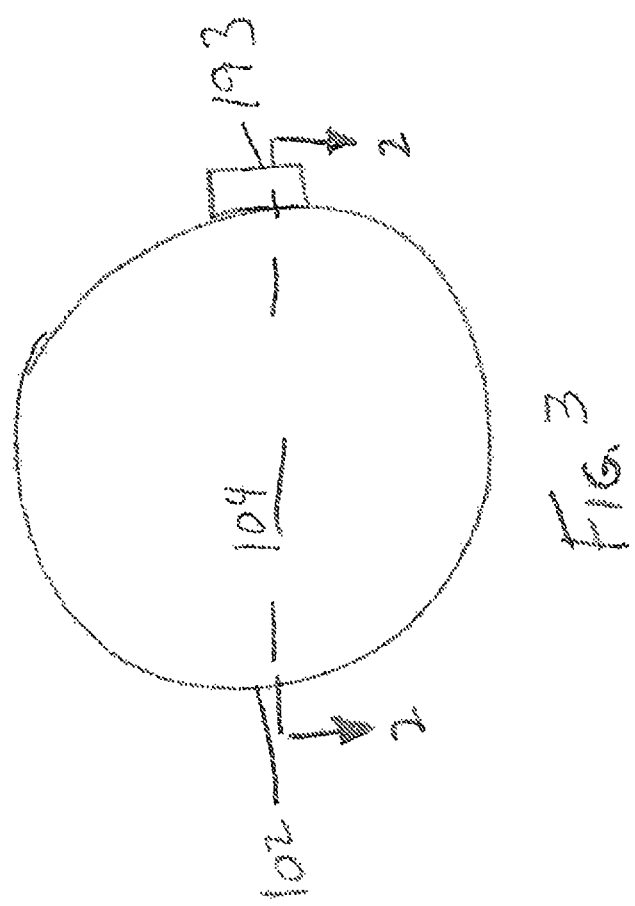
FIG. 3 is a top view of the air purification system of FIG. 1.
Figure 4:
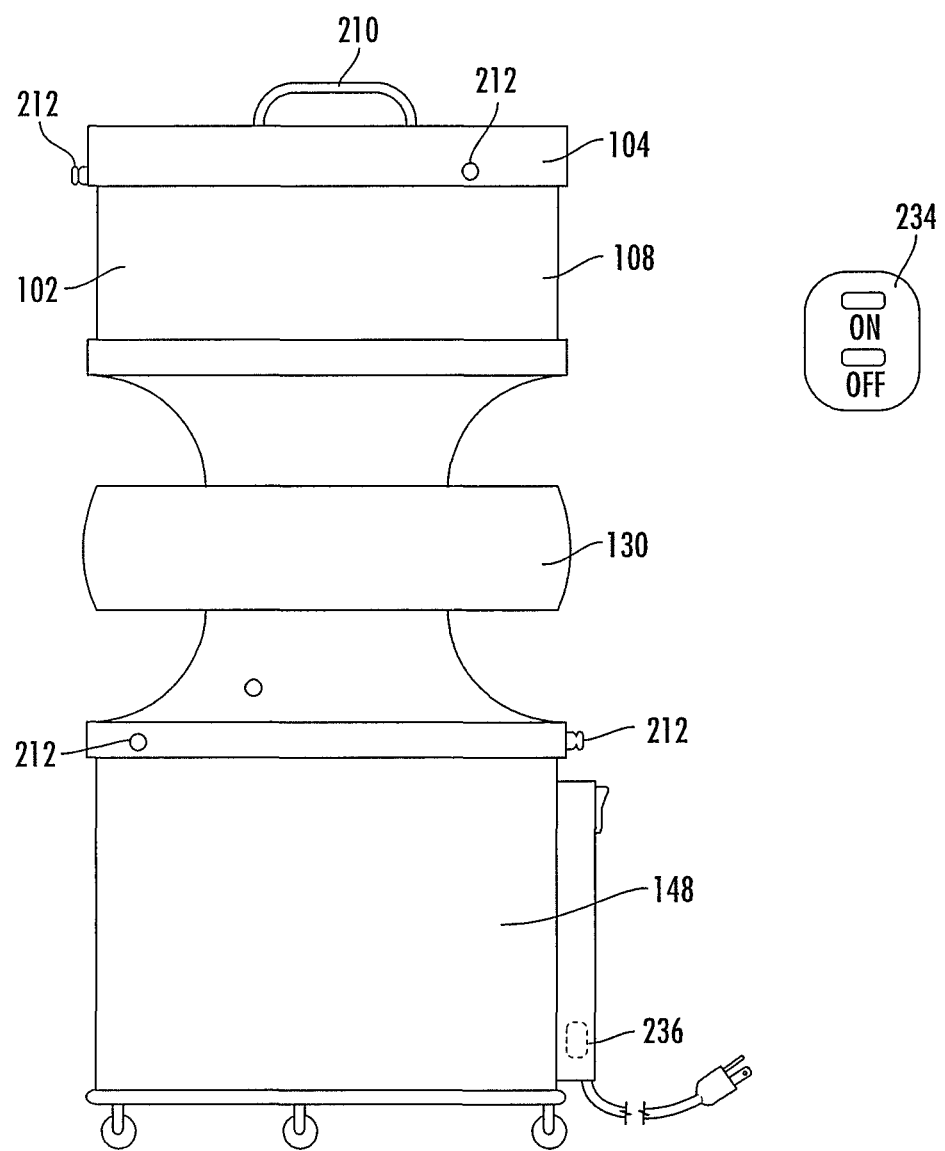
FIG. 4 is a front view of a modular, air purification assembly and remote control as described herein.

FIG. 1 is a front view of an embodiment of an air purification assembly 100 as described herein. FIG. 2 is a cross-sectional view of a portion of air purification assembly 100 taken along line 2-2 (shown in FIG. 1). Referring to FIGS. 1 and 2, in some embodiments, the air purification assembly 100 includes intake portion 102. In some embodiments, the intake portion 102 can include a substantially cylindrical intake portion 102, having a top portion 104, a bottom portion 106, and a sidewall portion 108 that extends from the top portion 104 to the bottom portion 106 such that there is a distance 109 from the top portion 104 to the bottom portion 106. In some embodiments, the distance 109 is 6 to 18 inches, or 6 to 10 inches, or 6.5 to 9 inches. While intake portion 102 is shown as being substantially cylindrical in FIG. 1, intake portion 102 can have any shape that enables the air purification assembly 100 to function as described herein.

Referring to FIG. 2, in some embodiments, sidewall portion 108 includes an exterior surface 110 and an interior surface 112 that is aligned a distance 114 from exterior surface 110, such that sidewall portion 108 creates a double wall. Defined within interior surface 112 of sidewall portion 108, is a channel 116 that extends from top portion 104 through bottom portion 106. Intake portion 102, in some embodiments, includes a plurality of first openings 118 on exterior surface 110 and second openings 119 through interior surface 112. As such, any fluid flow, such as air flow, can be received through openings 118, 119 and enter into channel 116. In some embodiments, the interior surface 112 is not necessary and is not included as part of the intake portion 102.

Referring to FIGS. 1 and 2, in some embodiments, a first extension portion, such as a substantially tubular flange 120, is coupled to intake portion 102. It should be noted that, as used herein, the term "couple" is not limited to a direct mechanical, thermal communication, and/or electrical connection between components, but may also include an indirect mechanical, thermal communication and/or electrical connection through multiple components. As shown in FIG. 2, flange 120 has a top portion 121 adapted to couple to a bottom portion 106 of intake portion 102 and flange 120 also has a bottom portion 122. Channel 116 can also extend through flange 120 from top portion 121 through bottom portion 122. While flange 120 is described and shown as being substantially tubular, flange 120 can have any suitable shape that enables air purification assembly 100 to function as described herein. As used herein, substantially tubular includes tubular-shaped members with uniform diameters, as well as, variable diameters, such as flanges 120, 141.

Referring to FIGS. 1 and 2, in some embodiments, a flow apparatus 124 is coupled to intake portion 102 via flange 120. In some embodiments, flow apparatus 124 also includes a top portion 126, a bottom portion 128, and a sidewall portion 130 that extends from top portion 126 to bottom portion 128. Top portion 126 of flow apparatus 124 can be coupled to bottom portion 122 of flange 120. In some embodiments, sidewall portion 130 has a solid, fluid impervious, exterior surface 132 and an opposing interior surface 134 such that fluid passing through channel 116 flows into flow apparatus 124 through a top portion 126 and exits flow apparatus 124 through bottom portion 128, as shown in FIG. 2.

As shown in FIG. 2, in some embodiments, flow apparatus 124 includes a fluid accelerator 136 (e.g., a ducted fan) positioned within channel 116. The fluid accelerator 136 can include a blade assembly 138 that includes a plurality of blades 140 that are permanently or removably coupled to blade assembly 138. In some embodiments, the blades 140 are configured to rotate within flow apparatus 124 such that a large volume of fluid flow, such as air flow, can efficiently or rapidly be channeled through air purification assembly 100 from the top portion 126 and exiting the bottom portion 12 of the flow apparatus 124.

Referring to FIGS. 1 and 2, in some embodiments, a second extension portion, such as a second substantially tubular flange 141, is coupled to flow apparatus 124. As shown in FIG. 2, flange 141 has a top portion 143 coupled to flow apparatus 124 and a bottom portion 143, wherein channel 116 also extends through flange top portion 142 and through flange bottom portion 143. While flange 141 is described and shown as being substantially tubular, flange 141 can have any suitable shape that enables air purification assembly 100 to function as described herein. The substantially tubular flanges 120, 141 can each independently have uniform or variable diameters. The variable diameter can taper so that the diameter decreases as the flange 120, 141 approaches the flow apparatus 124.

In some embodiments, a chamber portion 148 is coupled to flow apparatus 124 via flange 141. For example, chamber portion 148 has a top portion 150 that extends from or is coupled to bottom portion 144 of flange 141 and chamber portion 148 has a bottom portion 154. Channel 116 also extends through chamber portion 148 from top portion 150 to bottom portion 154. Chamber portion 148 includes a sidewall portion 156 that extends from top portion 150 to bottom portion 154 such that there is a distance 157 from top portion 150 to bottom portion 154. In some embodiments, distance 157 is approximately 6 to 30 inches, or 5 to 24 inches, or 6 to 18 inches, or 8 to 14 inches, or any combination of these ranges.

Similar to intake portion 102, referring to FIG. 2, sidewall portion 156 can include an exterior surface 160 and an interior surface 162 that is aligned a distance 164 from exterior surface 160 such that sidewall portion 156 creates a double wall. In some embodiments, distance 164 is one-half inch to six inches, or one inch to 4 inches, or one inch to 3 inches. In some embodiments, interior surface 162 is not present.

Channel 116 is defined within interior surface 162 of sidewall portion 156 or, where interior surface 162 is not present, within exterior surface 160 of the chamber portion 148. In some embodiments, an activated nonmetallic element, such as activated charcoal, is disposed between interior surface 162 and exterior surface 160. In some embodiments, the space between the interior surface 162 and the exterior surface 160, forms an activated charcoal bed. In some embodiments, chamber portion 148, includes a plurality of outer openings 170 in exterior surface 160 and a plurality of inner openings 171 in interior surface 162. As such, any flow, such as air flow, that is in channel 116 can exit from or leave air purification assembly 100 through openings 170 when appropriate pressure gradients (such as those produced by fluid accelerator 136) are applied. In some embodiments, the inner openings 171 are large enough that light from the UV light source 182 interacts with at least a portion of the activated charcoal bed 161, 226 disposed between the interior surface 162 and the exterior surface 160. In some embodiments, the inner openings 171 comprise, on average, at least 20% of the area of the interior surface 162, or at least 30% of the area of the interior surface 162, or at least 40% of the area of the interior surface 162.

In some embodiments, the activated charcoal bed can be formed from particulate activated charcoal (charcoal) or pelletized activated carbon (charcoal). In some embodiments, the diameter of the particles or pellets can range from 0.1 mm to 20 mm, or from 0.5 mm to 15 mm, or from 1 mm to 10 mm, or from 2 mm to 8 mm, or any combination of these ranges. In some embodiments, the length of the pellets can range from 0.1 mm to 40 mm, or from 0.5 mm to 20 mm, or from 1 mm to 15 mm, or from 2 mm to 10 mm, or any combination of these ranges.

In one embodiment, the air purification device 100 is designed to achieve excellent elimination of pathogens, including bacteria, even at high air velocities. It is believed that this is due to the area occupied by the inner openings 171 in combination with the relative position of the UV light source(s) 182 and the space 161 containing the activated nonmetallic materials. In particular, it is believed that the pathogens remain adhered to the surface of the activated nonmetallic materials being irradiated by the UV light (through the inner openings 171) well after the carrier air exits the air purification device 100. Thus, while the dwell time for the carrier air is relatively low, the dwell time of the pathogens adhered to the surface of the activated nonmetallic materials is sufficient for the UV light to eliminate, or kill, the pathogens.

In some embodiments, as shown in FIG. 1, chamber portion 148 includes a UV light assembly 180 that includes a UV light source 182. In some embodiments, UV light source 182 can be any type of UV lighting known in the art, such as a long cylindrical UV light tube, which can be positioned within channel 116 in chamber portion 148 such that UV light source 182 extends from proximate top portion 150 of chamber portion 148 to proximate bottom portion 154. In some embodiments, a first end 184 (e.g., a top end) of UV light source 182 can be coupled to chamber portion 148 using a first coupling device 185, such as a grommet or seat, and a second end 186 (e.g., a bottom end) of UV light source 182 can be coupled to chamber portion 148 using a second coupling device 187, such as a grommet or seat. As such, UV light source 182 is securely positioned within channel 116. Any other type of UV light source and/or orientation of the light source can be utilized that enables air purification assembly 100 to function as described herein.

The coupling devices 185, 187 used to support the UV light source(s) 182 described herein can be made of any type of suitable material adapted to hold the UV light source 182 in position while minimizing the likelihood of breaking the UV light source. Examples include, but are not limited to, plastic, elastomers, rubber materials, fabrics, woven materials, non-woven materials, and other similar materials.

A conduit 190 that is configured to transmit electrical current therein, such as an insulated metal wire, is coupled to an end, such as first end 184, of UV light source 182. Conduit 190 is also coupled to a control device 192 such that control device 192 is coupled to UV light source 182 via conduit 190. In some embodiments, chamber portion 148 includes an enclosure portion 193 that is coupled to exterior surface 160 of chamber portion 148, wherein enclosure portion 193 is configured to substantially enclose control device 192 therein. In some embodiments, control device 192 can be a standard UV electrical ballast that is configured to control the amount of current being used by UV light source 182, such as by using an electrical load (not shown). In some embodiments, an electrical cord can be coupled to ballast to provide electricity from an external electricity source (e.g., a AC or DC current supplied from a residential or commercial source or a generator). As used herein, a generator is intended to encompass any motor capable of producing and distributing electricity to an external source. Thus, generator is intended to encompass combustion engines, turbine engines, and other engines used to generate electricity for vehicles (planes, boats, ships, automobiles, etc.).

In some embodiments, air purification assembly 100 includes a stand portion 194 having a first surface 196 that is coupled to a plurality of wheels 197 and a second surface 198 that that is coupled to a bottom portion 150 of chamber portion 148. Wheels 197 (e.g., casters) enable a user to easily move air purification assembly 100 to various different locations within an indoor or outdoor space or vehicle. In some embodiments, air purification assembly 100 can include a handle that is coupled to top portion 104 of intake portion 102 such that a user can easily hold or grip air purification assembly 100.

In some embodiments, chamber portion 148 includes at least one top opening 200 that can extend from a top portion 150 of the chamber portion 148. The top opening(s) 200 can provide access to the space 161, e.g., the charcoal bed between the interior surface 162 and the exterior surface 160. As such, a user can refill the space 161 with the activated nonmetallic element using the at least one top opening 200. The space 161 can be filled with the activated nonmetallic element in a granular form (e.g., a charcoal bed), as a filter media with granules embedded or adhered onto it, or using other techniques known in the art. In some embodiments, top the opening 200 can be substantially covered or closed via a cap 201. In some embodiments, air purification assembly 100 can also include an indicator 202, such as a light-emitting diode (LED) or other indicator known in the art, that can indicate to the user when the level for the activated nonmetallic element within chamber portion 148 is substantially low or below a predefined threshold. The air purification assembly 100 can also include a second indicator 204 that illuminates when the fluid accelerator 136 is on.

As shown in the Figures, air intake section 102, flange 120, flow apparatus 124, flange 141, chamber portion 148, and stand portion 194 can be stacked on top of one another such that the overall height of air purification assembly 100 is dependent on the size of each of the aforementioned components. In some embodiments, the overall height of air purification assembly 100 is from 8 to 60 inches, or from 16 to 54 inches, or from 24 to 48 inches.

In some embodiments, each of the components of air purification assembly 100, such as air intake section 102, flange 120, flow apparatus 124, flange 141, chamber portion 148, and stand portion 194, including wheels 197, are secured together such that air purification assembly 100 is a single unitary component. Alternatively, one or more of the aforementioned components may be formed separately then removably or permanently coupled together. Each of air intake section 102, flange 120, flow apparatus 124, flange 141, chamber portion 148, and stand portion 194 can be formed via a variety of manufacturing processes known in the art, including, but not limited to, molding processes, drawing processes, machining processes, or others.

One or more types of materials may be used to fabricate air purification assembly 100 and the aforementioned components. For example, the exterior portions of air intake section 102, flange 120, flow apparatus 124, flange 141, chamber portion 148, and stand portion 194, can be formed with materials that are selected based on suitability for one or more manufacturing techniques, dimensional stability, cost, moldability, workability, rigidity, and/or other characteristic of the material(s). In some embodiments, at least the exterior portions of air intake section 102, flange 120, flow apparatus 124, flange 141, chamber portion 148, and stand portion 194 can be at least partially formed from a metallic material, such as steel, aluminum, or combinations or variations thereof. In some embodiments, at least the exterior portions of air intake section 102, flange 120, flow apparatus 124, flange 141, chamber portion 148, and stand portion 194 can be formed from the same material(s). Alternatively, different and varying materials may be used to form at least the exterior portions of each of the aforementioned components.

During use, a user can position air purification assembly 100 in any type of environment, such as a living space, a working space, or a vehicle and/or within a cabinet that may be in such an environment. When positioned in such an environment, fluid flow, such as air flow, being circulated within the environment can flow through air purification assembly 100. For example, contaminated air flow that includes, for example, air contaminated with odors, viruses, stale air, mold, and/or mildew can flow through first openings 118 of intake section 102 and into channel 116. The contaminated air flow then flows into flow apparatus 124, wherein fluid accelerator 136 accelerates a large volume of the contaminated air flow through channel 116 and into flange 141 and then into chamber portion 148.

When flowing through the chamber portion 148, the contaminated air flow is exposed to the UV light emitted by UV light source 182 such that contaminants within the airflow, such as viruses and/or bacteria, can be killed or neutralized. As the contaminated air flow exits the channel 116 and enters the space 161, the contaminated air flow reacts with the activated nonmetallic element, such as activated charcoal, such that at least some of the remaining contaminants in the air flow are being filtered out, captured, or neutralized. Moreover, the double wall formed as a result of the distance 164 between exterior surface 160 and interior surface 162, and the activated nonmetallic element disposed therebetween, inhibits UV light from escaping the chamber portion 148 and causing damage to occupants of the environment around the air purification assembly 100. After contacting the activated nonmetallic element and being exposed to UV light source 182, the contaminated air has been purified and decontaminated and exits the air purification assembly 100 via second openings 170 of the chamber portion 148.

In some embodiments, the activated nonmetallic element can be present in a sufficient quantity and positioned within the space 161 such that pathogens contacting the activated nonmetallic element interact with (e.g., adhere to) the activated nonmetallic element long enough that the UV light emitted by the UV light source 182 eliminates (e.g., neutralizes or kills) the pathogens in the air passing through the air purification assembly 100. In some embodiments, at least 80% of a pathogen is eliminated, or at least 85% of a pathogen is eliminated, or at least 90% of a pathogen is eliminated, or at least 95% of a pathogen is eliminated, or at least 98% of a pathogen is eliminated, or at least 99% of a pathogen is eliminated, or at least 99.9% of a pathogen is eliminated, or at least 99.99% of a pathogen is eliminated.

In some embodiments, these elimination rates are achieved within 200 circulations of the volume of the room, 160 circulations of the volume of the room, or within 120 circulations of the room, or within 80 circulations of the volume of the room, or within 70 circulations of the room, or within 60 circulations of the room. As used herein, "eliminate" is used to indicate a reduction in the number of colony forming units (CFUs) of the indicated magnitude within a given period of time. Examples of pathogens of interest include, but are not limited to, *Clostridium difficile, Enterococcus faecalis, Pseudomonas aeruginosa, Staphylococcus aureus*, and *Streptococcus* species.

Figure 5:
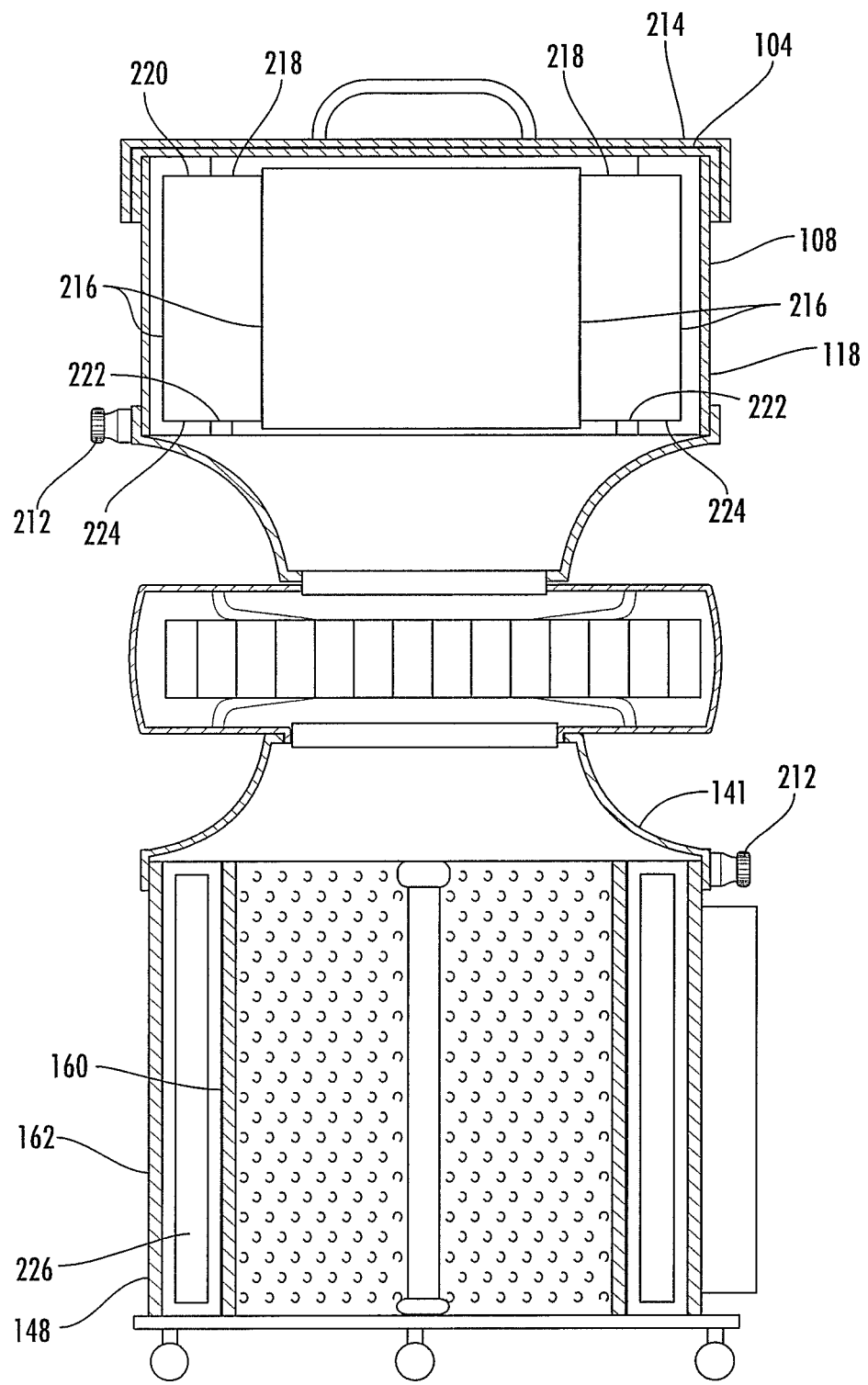
FIG. 5 is a cross-sectional view of the air purification assembly shown in FIG. 4 taken along a cut line equivalent to 2-2 of FIG. 3.
Figure 6:
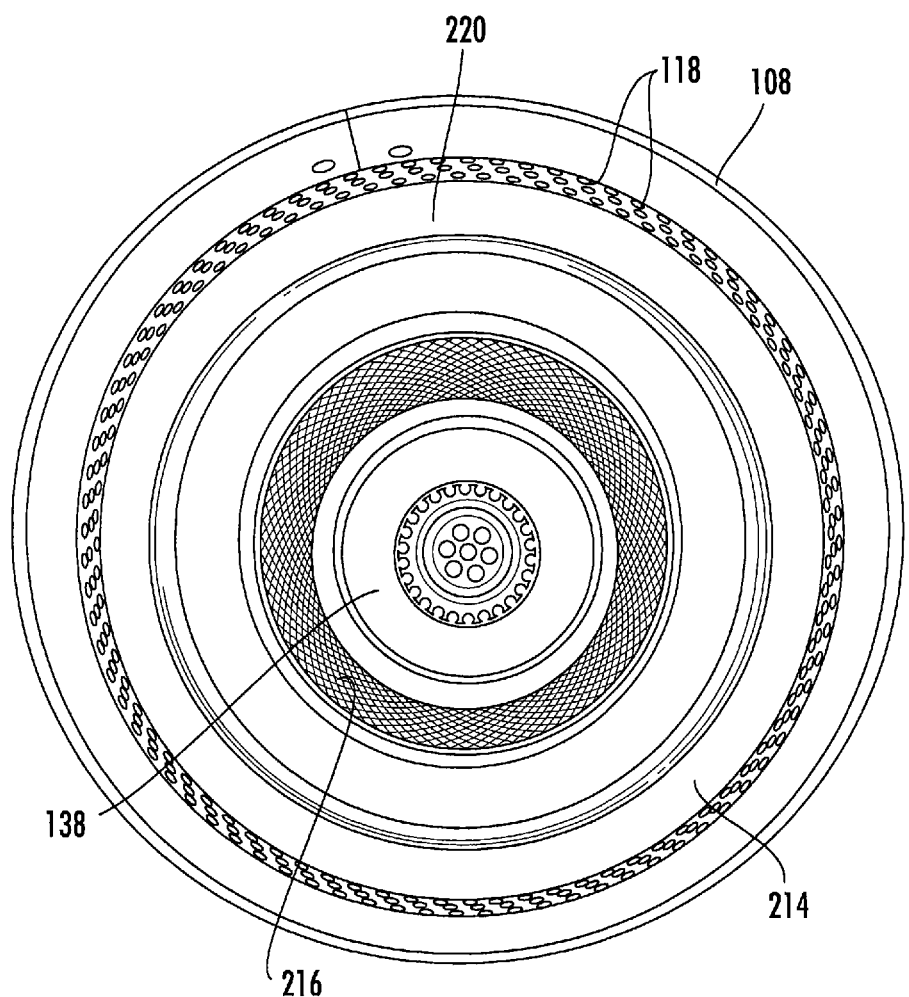
FIG. 6 is a top view of the intake portion with the lid removed to expose the filter cartridge.
Figure 7:
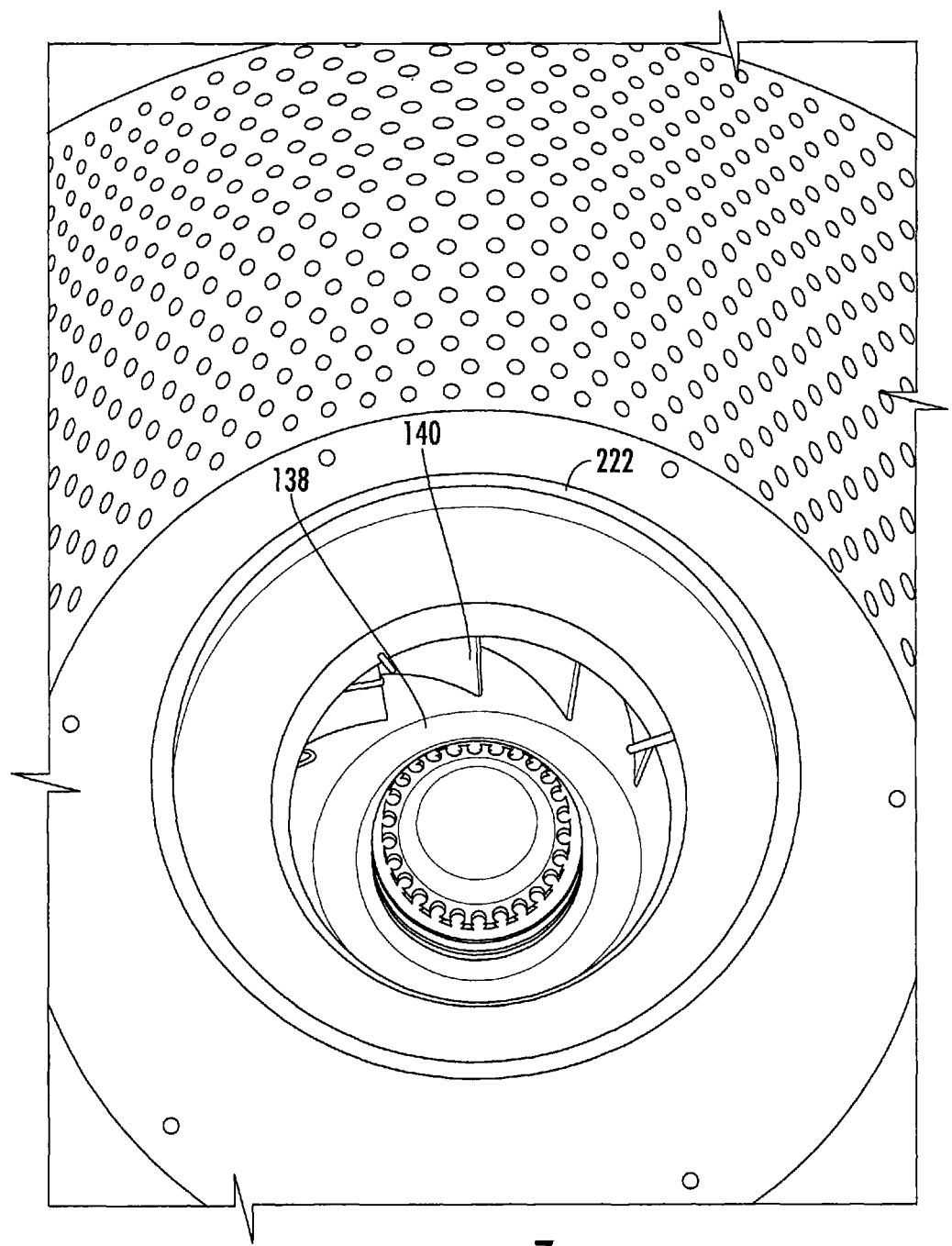
FIG. 7 is a top, perspective view of the interior of the intake portion of FIG. 6, with the filter cartridge removed.
Figure 8:
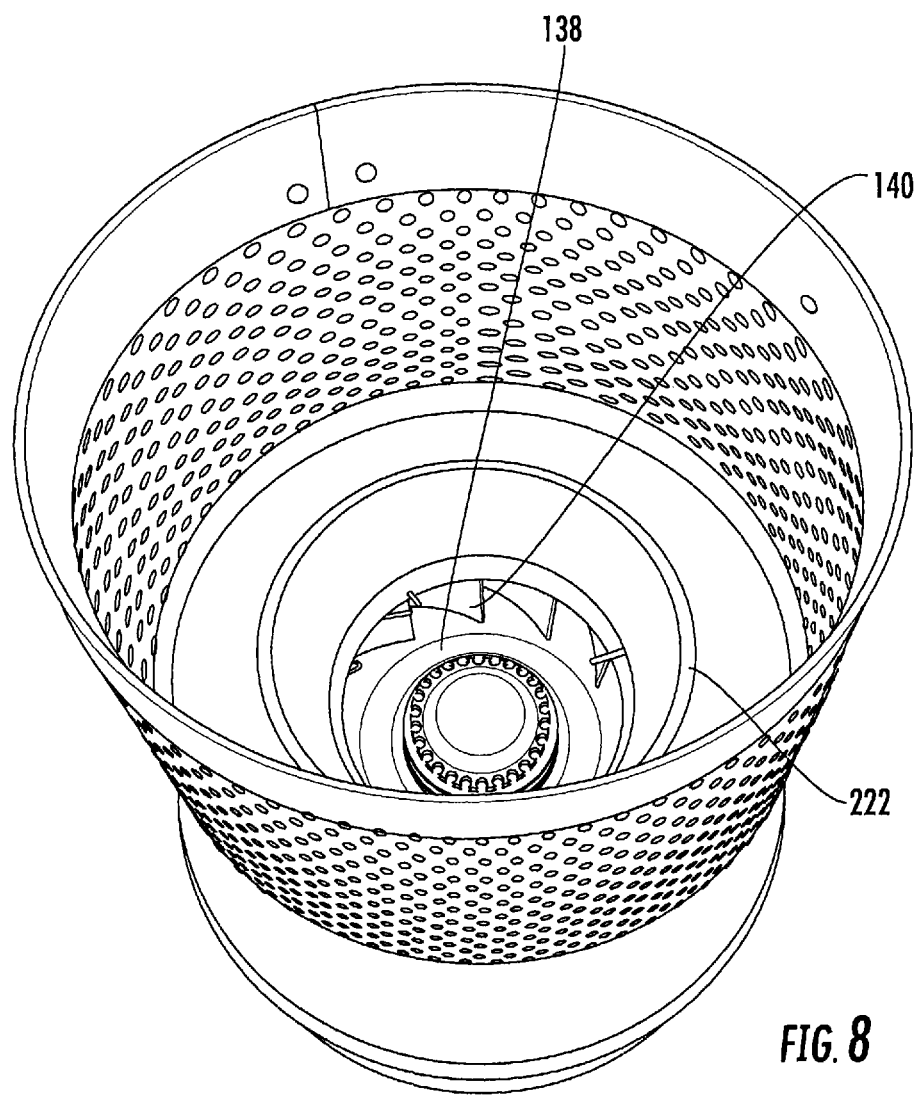
FIG. 8 is a close-up view of FIG. 8.
Figure 9:
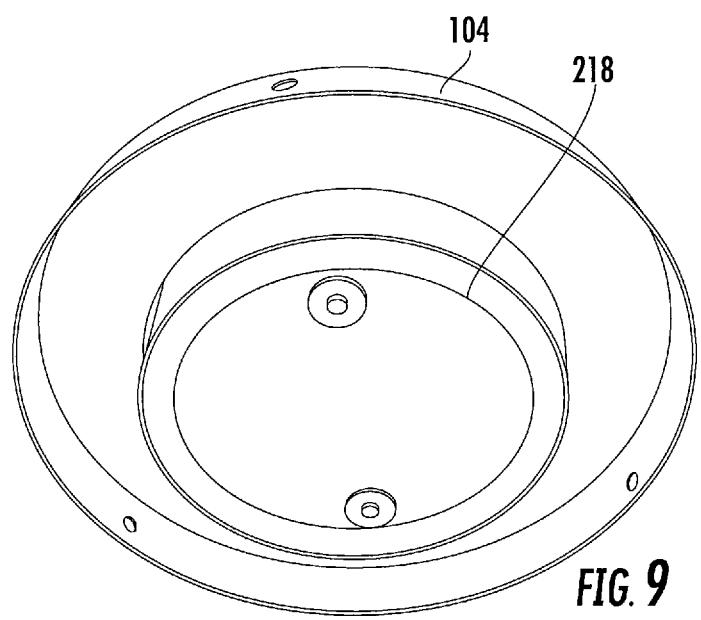
FIG. 9 is a bottom view of a lid to the intake portion of FIG. 6.
Figure 10:
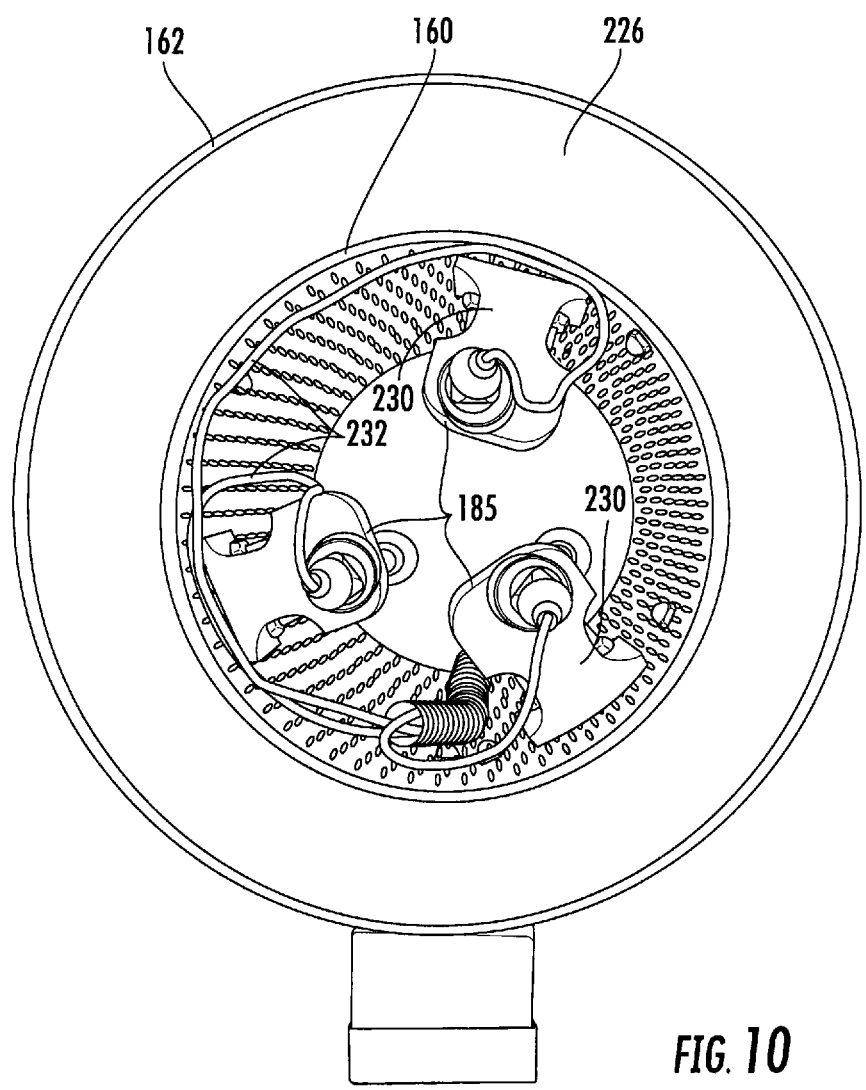
FIG. 10 is a top view of an interior of the chamber portion once the flange has been removed.
Figure 11:
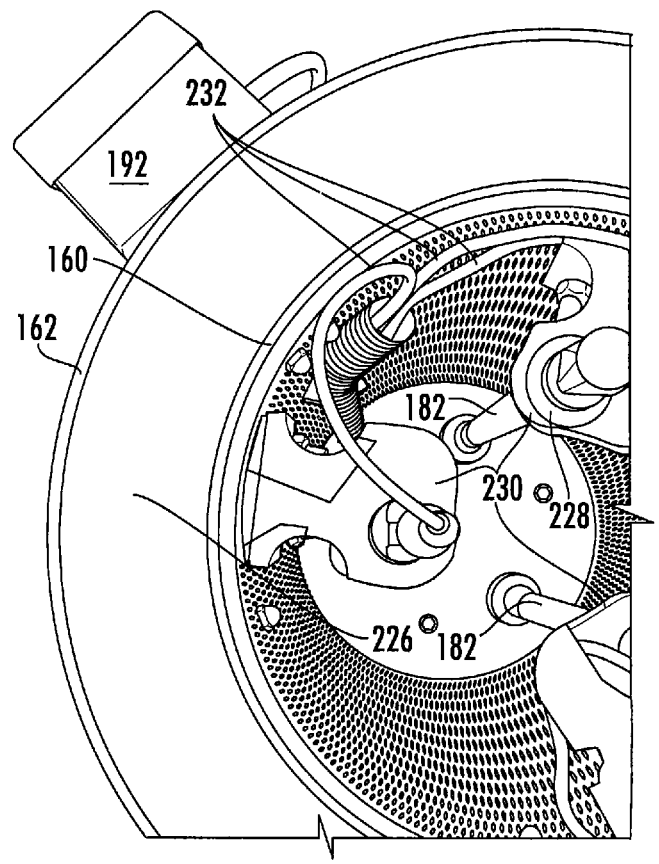
FIG. 11 is a close-up view of the chamber portion of FIG. 10.
Figure 12:
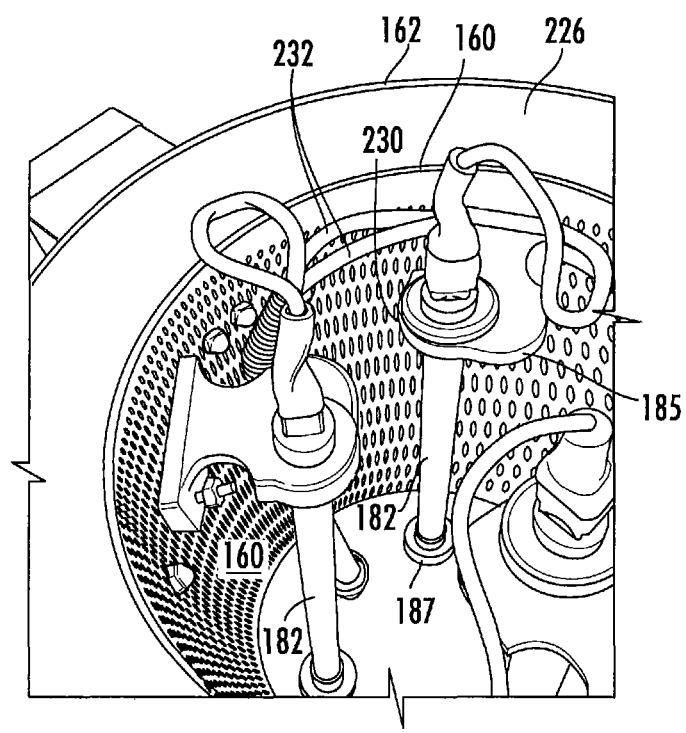
FIG. 12 is an elevation view of the chamber portion of FIG. 10.
Figure 13:
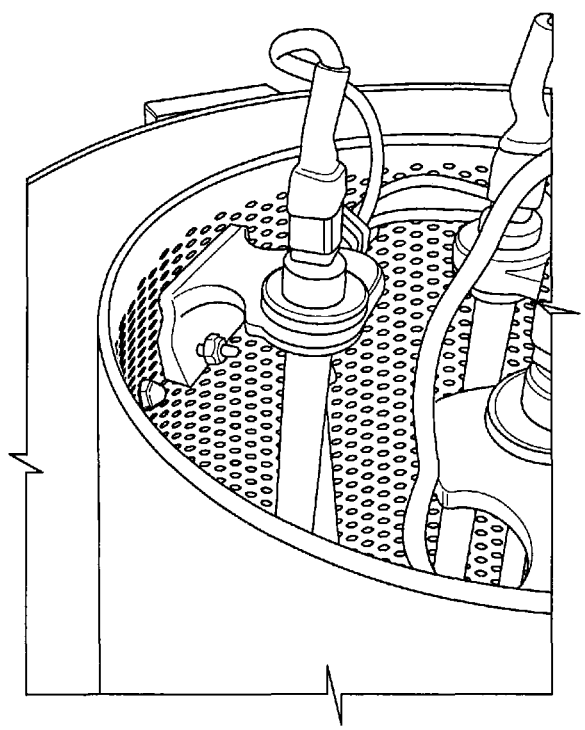
FIG. 13 is a close-up front, elevation view of the chamber portion of FIG. 10.

As used herein, the number of circulations of the room is calculated by dividing the volume per minute moved by fan by the volume of room and multiplying by the length of time the fan is operating. For example, for a fan blowing 470 cubic feet per minute in a 7' cube-shaped room (343 cubic feet), the number of circulations of the room in one hour would be (470/343)*60, or just over 82 circulations. In some embodiments, as shown in FIGS. 5-13, the top portion 104 can be a removable lid, which can include a handle 210. The removable lid 104 can be secured to the sidewall portion 108 via a set screw 212. In some embodiments, the intake portion 102 includes a filter cartridge 214. In some embodiments the cartridge filter 214 can be a HEPA filter. In some embodiments, the filter can be a charcoal or carbon air filter. In some embodiments, as shown in FIGS. 5-6, the filter cartridge 214 can be a generally cylindrical pleated filter adapted for air to flow through the longitudinal sides 216. In such embodiments, the sidewall portion 108 may be a single walled sidewall portion 108, where the generally cylindrical cartridge fits within the perforated, exterior surface 110.

In some embodiments, as shown in FIGS. 5-9, the intake portion 102 is adapted so that, when assembled, air flowing into the intake portion through the openings 118 is directed sequentially from the outer to the inner longitudinal side 216 of the filter cartridge and into the channel 116. In some embodiments, a surface of the lid 104 includes a lid seal 218 adapted for contacting and creating a seal with an upper surface 220 of the filter cartridge 214 and a sealing surface 222 of the intake portion 102 contacts a lower surface 224 of the filter cartridge 214. In this way, the seals effectively force all air to pass through the longitudinal sides 216 of the filter cartridge 214 before entering the channel 116. In addition, the filter media can be selected to effective block any UV light that escapes from the chamber portion 148 into the intake portion 102.

In some embodiments, as shown in FIGS. 4-5 and 10-13, the lower flange 141 is removably coupled to the chamber portion 148. For example, the lower flange 141 can be secured to the chamber portion 148 by one or more set screws 212. In such embodiments, a filter media or charcoal bed 226 can be positioned within the space 161 between the interior surface 162 and the exterior surface 160. In some embodiments, the filter media 226 can be a cartridge filter (e.g., a cylindrical cartridge filter), while in other embodiments, the filter media be in sheet form (e.g., a non-woven including charcoal or activated carbon). In this arrangement, the flange 141 can be removed from the chamber portion 148 and the filter media 226 can be quickly and easily removed from and replaced in the space 161.

As shown in FIGS. 10-13, in some embodiments, the first coupling device 185 can be an opening 228 in a support bracket 230 mounted to the interior surface 162 of the chamber portion 148. In such embodiments, as shown in FIGS. 10-13, the second coupling device 187 can be a seat. As shown in FIGS. 10-13, in some embodiments at least two or at least three UV light sources 182 can be positioned within the portion of the channel 116 passing through the center of the chamber portion 148. An electrical support cord 232 in electrical communication with the electrical control device 192 can be attached to each UV light source 182.

In some embodiments, the system also includes a remote control 234 and the air purification device 100 includes a wireless receiver 236 to receiving signals from the remote control 234 and transmitting them to the electrical control device 192. In some embodiments, the wireless receiver 236 can be located within the enclosure portion 193.

In some embodiments, the air purification device 100 can be used in an environment where hospital acquired infections (HAI) can be present. In any environment, including HAI situations, the filter cartridge 214 can include HEPA filter functionality, while the filter media 226 can be an activated carbon or charcoal filter media (e.g., a non-woven material including activated carbon or charcoal). In such embodiments, the UV light can be used to kill germs and pathogens, as well as, eradicate undesirable odors.

Various embodiments of the assembly and method are described above in detail. The assembly and method are not limited to the specific embodiments described herein, but rather, components of each assembly and/or method may be utilized independently and separately from other components described herein. For example, each assembly may also be used in combination with other assemblies and is not limited to practice with only systems as described herein. Rather, the exemplary embodiment can be implemented and utilized in connection with many other applications.

Although specific features of various embodiments of the disclosure may be shown in some drawings and not in others, this is for convenience only. In accordance with the principles of the invention, any feature of a drawing may be referenced and/or claimed in combination with any feature of any other drawing.

EXAMPLES

A study was conducted to determine the efficacy of the air purification assembly described herein for the elimination of airborne pathogens. The air purification assembly used was similar to that shown in FIGS. 4 & 5, with the three UV light source arrangement shown in FIGS. 10-12. The fan used was adapted to intake up to 470 CFM of indoor air through the devices' upper HEPA filtration chamber, and down through a second chamber, that contained a spectrum 254 category UVC bulb array, to kill bacteria at a high level of efficacy. The air is passed through a pelletized activated charcoal bed (4 mm diameter×6 mm length) that encircles the lower chamber, for odor elimination. The overall height is measured at 37.00" and the maximum diameter is 12.00". The external diameter of the upper chamber is 12.00" and it is 8.50" tall. This chamber is provided with a cover at both the upper and lower end. The external wall of this chamber is constructed of a perforated metal sheet. Internally, it has a HEPA filtration system. The central chamber (4.00" in height) connects the upper and lower chamber and, externally, it has a switch to adjust the airflow. The lower chamber is 13.50" in height, the upper end of this is connected to the lower part of the central chamber and the lower part of this chamber rests on the four wheel ring stand (this can be 3 wheels, 5 wheels, or more wheels in other embodiments). Externally, it appears as a perforated sheet while internally, it contains a carbon filtration wrap.

The study was conducted by introducing an aerosilized sample of the relevant bacteria to an enclosed environment in the form of a 7 foot cubic volume. Samples were taken from the closed environment after being circulated by the air purification assembly for the indicated time and these samples were tested. Measurements indicated as pretreatment are taken without operating the air purification assembly, while measurements indicated as post treatment were taken after the air purification assembly was operated for the indicated period of time.

The study analyzed the efficacy of the air purification system against *enterococcus faecalis, pseudomonas aeruginosa* American Type Culture Collection (ATCC), *staphylococcus aureus* ATCC, and *streptococcus* species ATCC.

Tables 1 & 2, below, show the results:

TABLE 1

| Treatment | Hour | Sample Set | Concentration (CFU/m3) | Average | Hourly Difference (CFU/m3) | Hourly Reduction (%) | Hourly Log Reduction | Total Reduction (%) | Total Reduction (Log) |
|---|---|---|---|---|---|---|---|---|---|
| Pretreatment | 0 | I | 43500000 | 42200000 | — | — | — | 94.16 | 1.23 |
|  |  | II | 40900000 |  |  |  |  |  |  |
|  | 1 | I | 11200000 | 9585000 | 32515000 | 77.05 | 0.64 |  |  |
|  |  | II | 8170000 |  |  |  |  |  |  |
|  | 2 | I | 2510000 | 2465000 | 7220000 | 74.55 | 0.59 |  |  |
|  |  | II | 2420000 |  |  |  |  |  |  |
| Post Treatment | 0 | I | 38970000 | 41685000 | — | — | — | 100.00 | — |
|  |  | II | 44400000 |  |  |  |  |  |  |
|  | 1 | I | 0 | 0 | 41685000 | 100.00 | — |  |  |
|  |  | II | 0 |  |  |  |  |  |  |
|  | 2 | I | 0 | 0 | 0 | — | — |  |  |
|  |  | II | 0 |  |  |  |  |  |  |

TABLE 2

| Treatment | Hour | Temperature | Growth Media | Incubation Period | Sample Set | *Enterococcus faecalis* | *Pseudomonas aeruginosa* | *Staphylococcus aureus* | *Streptococcus* species | Remarks |
|---|---|---|---|---|---|---|---|---|---|---|
| Pre | 0 | 30° ± 2° C. | TSA | 112 hours | I | ++++ | ++++ | ++++ | ++++ |  |
|  |  |  |  |  | II | ++++ | ++++ | ++++ | ++++ |  |
|  | 1 |  |  |  | I | ++++ | ++++ | ++++ | ++++ |  |
|  |  |  |  |  | II | ++++ | ++++ | ++++ | ++++ |  |
|  | 2 |  |  |  | I | +++ | +++ | +++ | +++ |  |
|  |  |  |  |  | II | +++ | +++ | +++ | +++ |  |
| Post | 0 |  |  |  | I | ++++ | ++++ | ++++ | ++++ |  |
|  |  |  |  |  | II | ++++ | ++++ | ++++ | ++++ |  |
|  | 1 |  |  |  | I | − | − | − | − | − |
|  |  |  |  |  | II | − | − | − | − | − |
|  | 2 |  |  |  | I | − | − | − | − | − |
|  |  |  |  |  | II | − | − | − | − | − |

In Table 2, "++++" represents greater than 1500 colony forming units (CFU), "+++" represents 1001 to 1500 CFU, and "−" represents no CFU detected. Tables 1 & 2 shows that air contaminated with large amounts of *enterococcus faecalis, pseudomonas aeruginosa* American Type Culture Collection (ATCC), *staphylococcus aureus* ATCC, and *streptococcus* species ATCC no longer exhibited any colony forming units of these bacteria after one hour of exposure to the air purification system.

Thus, the air purification system provides excellent elimination of airborne bacteria, especially, *enterococcus faecalis, pseudomonas aeruginosa* American Type Culture Collection (ATCC), *staphylococcus aureus* ATCC, and *streptococcus* species ATCC. Based on the high volume of air moved by the fan in the air purification system, the dwell time in the lower chamber is not believed to be sufficient to achieve this level of performance. Thus, it is believed that the high elimination rates are a function of a secondary mechanism. While not wishing to be bound by theory, it is believed that the bacteria are adsorbed to the surface of the activated carbon (activated nonmetallic material) in the lower chamber, which increases the time during which the bacteria are exposed to the UV light relative to bacteria that remain entrained in the air passing through the air purification system. Thus, it is believed that one reason the air purification systems described herein can eliminate airborne bacteria even at high flow rates is the relative position of the activated carbon with respect to the UV light and the large perforations 171 in the interior surface 162 of the chamber portion 148.

This written description uses examples to describe the disclosure, including the best mode, and also to enable any person skilled in the art to practice the invention, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of producing purified air from contaminated air, wherein said method comprises:
    receiving a contaminated air flow through a plurality of first openings in a surface of an intake;
    channeling the contaminated air flow into the air purification assembly via a flow apparatus that is coupled to the intake;
    channeling the contaminated air flow to a chamber portion comprising a bed of activated nonmetallic element and a ultraviolet (UV) light assembly;
    purifying the contaminated air flow when the contaminated air flow passes through the bed of activated nonmetallic element and past the ultraviolet (UV) light assembly, wherein said bed of activated nonmetallic element and said ultraviolet (UV) light assembly are adapted so that an upstream surface of the bed of activated nonmetallic element is irradiated by UV light emitted by said ultraviolet light assembly to produce decontaminated air; and
    channeling the decontaminated air into a living space.

2. The method in accordance with claim 1, further comprising channeling the contaminated airflow through a channel that extends from a portion of the intake to a portion of the chamber portion.

3. The method in accordance with claim 1, wherein the activated nonmetallic element includes charcoal.

4. The method in accordance with claim 1, wherein channeling the contaminated air flow efficiently through the air purification assembly comprises channeling the contaminated air flow efficiently through the air purification assembly via a cylindrical duct and a blade assembly that is mounted within the cylindrical duct.

5. The method in accordance with claim 1, wherein channeling the contaminated air flow to a chamber portion comprises channeling the contaminated air flow to a chamber portion that includes an interior surface such that the activated nonmetallic element is positioned on at least a portion of the interior surface.

6. A method of producing purified air from contaminated air, wherein said method comprises:
    receiving contaminated air;
    channeling the contaminated air to a chamber portion comprising a bed of activated nonmetallic element and a ultraviolet (UV) light assembly;
    purifying the contaminated air when the contaminated air is channeled through the bed of activated nonmetallic element, wherein said bed of activated nonmetallic element and said ultraviolet (UV) light assembly are positioned so that at least a portion of the bed of activated nonmetallic element is irradiated by UV light emitted by said ultraviolet light assembly to produce decontaminated air; and
    channeling the decontaminated air into a living space.

7. The method in accordance with claim 6, further comprising channeling the contaminated airflow through a channel that extends into the chamber portion.

8. The method in accordance with claim 6, wherein the bed of activated nonmetallic element comprises charcoal.

9. The method in accordance with claim 6, wherein the bed of activated nonmetallic element comprises activated carbon.

10. The method in accordance with claim 6, wherein channeling the contaminated air flow through the bed of activated nonmetallic element is facilitated by a cylindrical duct and a blade assembly that is mounted within the cylindrical duct.

11. The method in accordance with claim 6, wherein channeling the contaminated air flow through the bed of activated nonmetallic element comprises channeling the contaminated air flow onto an upstream surface of the bed of activated nonmetallic element and the UV light assembly is positioned to irradiate the upstream surface of at least a portion of the bed of activated nonmetallic element.

12. The method in accordance with claim 11, wherein the bed of activated nonmetallic element has a tubular shape and the UV light is positioned to irradiate an inner surface of the tubular shape, wherein the inner surface is the upstream surface.

13. A method of producing purified air from contaminated air, wherein said method comprises:
    receiving contaminated air;
    channeling the contaminated air through a bed of activated nonmetallic element;
    purifying the contaminated air when the contaminated air is channeled through the bed of activated nonmetallic element, wherein an ultraviolet (UV) light assembly is positioned so that at least a portion of the bed of activated nonmetallic element is irradiated by UV light emitted by said ultraviolet light assembly to produce decontaminated air; and
    channeling the decontaminated air into a living space.

14. The method in accordance with claim 13, further comprising channeling the contaminated airflow through a channel fluidically coupled to the bed of activated nonmetallic element.

15. The method in accordance with claim 13, wherein the bed of activated nonmetallic element comprises charcoal.

16. The method in accordance with claim 13, wherein the bed of activated nonmetallic element comprises activated carbon.

17. The method in accordance with claim 13, wherein channeling the contaminated air flow through the bed of activated nonmetallic element is facilitated by a cylindrical duct and a blade assembly that is mounted within the cylindrical duct.

18. The method in accordance with claim 13, wherein channeling the contaminated air flow through the bed of activated nonmetallic element comprises channeling the contaminated air flow onto an upstream surface of the bed of activated nonmetallic element and the UV light assembly is positioned to irradiate the upstream surface of at least a portion of the bed of activated nonmetallic element.

19. The method in accordance with claim 18, wherein the bed of activated nonmetallic element has a tubular shape and the UV light is positioned to irradiate an inner surface of the tubular shape, wherein the inner surface is the upstream surface.

20. The method in accordance with claim 18, wherein the decontaminated air exits the bed of activated nonmetallic element through a downstream surface, distinct from the upstream surface.

* * * * *